United States Patent
Denieul et al.

(10) Patent No.: US 8,249,818 B2
(45) Date of Patent: Aug. 21, 2012

(54) METHOD FOR QUALIFYING THE VARIABILITY OF AN EFFLUENT COMPOSITION

(75) Inventors: Marie-Pierre Denieul, Clichy (FR); Olivier Daniel, Lognes (FR); Arnaud Bucaille, Colombes (FR); Cyrille Lemoine, Sartrouville (FR)

(73) Assignee: Veolia Eau—Compagnie Generale des Eaux, Paris (FR)

( * ) Notice: Subject to any disclaimer, the term of this patent is extended or adjusted under 35 U.S.C. 154(b) by 427 days.

(21) Appl. No.: 12/523,890

(22) PCT Filed: Jan. 24, 2008

(86) PCT No.: PCT/FR2008/050110
§ 371 (c)(1),
(2), (4) Date: Jan. 13, 2010

(87) PCT Pub. No.: WO2008/104647
PCT Pub. Date: Sep. 4, 2008

(65) Prior Publication Data
US 2010/0125422 A1    May 20, 2010

(30) Foreign Application Priority Data
Jan. 25, 2007  (FR) ..................................... 07 52882

(51) Int. Cl.
*G01N 31/00* (2006.01)
(52) U.S. Cl. ........................................................ 702/25
(58) Field of Classification Search ................... 702/25, 702/182–185
See application file for complete search history.

(56) References Cited

U.S. PATENT DOCUMENTS

| | | | |
|---|---|---|---|
| 5,870,692 A | 2/1999 | Millo | |
| 6,351,986 B1 | 3/2002 | Schwab | |
| 2003/0236649 A1 | 12/2003 | Kodukula | |
| 2010/0204924 A1* | 8/2010 | Wolfe et al. | ..................... 702/25 |

FOREIGN PATENT DOCUMENTS

| | | |
|---|---|---|
| DE | 19645246 | 10/1996 |
| EP | 0707247 | 4/1996 |
| EP | 1070954 | 1/2001 |
| FR | 2783322 | 3/2000 |
| FR | 2787883 | 6/2000 |
| WO | wo 98/40721 | 9/1998 |

OTHER PUBLICATIONS

The International Search Report corresponding to the PCT/FR2008/050110 application dated Sep. 9, 2008.

\* cited by examiner

*Primary Examiner* — Edward Raymond
(74) *Attorney, Agent, or Firm* — Kilpatrick Townsend & Stockton LLP

(57) ABSTRACT

The invention relates to a method of qualifying the variability of the composition of an effluent, in which method a series of measurements is effected over time of at least one first and one second parameter of the effluent. The invention is characterized in that, in each time step, first and second derivatives of the parameters are determined, first and second logical domains are defined, probabilities of the first derivatives belonging to the first logical domains are assigned, probabilities of the second derivatives belonging to the second logical domains are assigned, global logical domains are defined, global probabilities of belonging to the global logical domains are assigned, and the variability of the composition of the effluent is qualified on the basis of these global probabilities of belonging to the global logical domains.

20 Claims, 2 Drawing Sheets

METHOD FOR QUALIFYING THE VARIABILITY OF AN EFFLUENT COMPOSITION

This application is a National Stage of International Application No. PCT/FR2008/050110, filed Jan. 24, 2008, which claims the benefit of French Patent Application No. 0752882, filed Jan. 25, 2007, the disclosure of both applications being incorporated herein by reference in their entirety.

The present invention relates to the field of analysis and on-line control of the composition of liquid or gaseous effluents, such as drinking water, urban waste water, or industrial waste water, for example.

The present invention relates more particularly to a method of detecting the variability of the composition of such a liquid or gaseous effluent.

In detection methods known in the art, measurements are effected in-line, for example in a pipe on the upstream side of a waste water treatment station.

Such a method detects any abnormality in the composition of the effluent, notably any physical-chemical or biological abnormality, liable to cause an incident in the treatment process downstream of the location at which the measurements are effected.

Acquiring these measurements in-line and processing them mathematically alerts the operator to the arrival of effluent having a composition different from that of the effluent usually feeding the treatment station. If necessary, the operator can take appropriate measures, for example by diverting the "different" effluent to another treatment unit and/or taking a sample of the effluent to be analyzed a posteriori.

Some on-line methods of detecting the variability of an effluent use visible ultra-violet (VIS-UV) spectrophotometry to represent the qualitative variability of the effluent on the basis of a set of signals.

For the qualitative aspects, the VIS-UV spectrum serves as a "fingerprint" of the effluent.

In other words, a given effluent has its own VIS-UV spectrum comprising particular points (known as isobestic points) which, in theory, do not vary over time.

It is clear that, as soon as a change is detected in the UV spectrum as measured in-line, the change reflects a modification to the composition of the effluent.

The information obtained indicates to the operator whether the overall quality of the effluent is maintained or not, but there is no provision for evaluating the hazard presented by the effluent. Finally, these points do not necessarily exist for all effluents, which usually renders the method ineffective.

As described in the documents FR 2 783 322 and FR 2 787 883, another known method of processing UV spectra uses deconvolution of the UV spectra, based on the assumption that each UV spectrum of an effluent can be considered as a linear combination of a small number of known UV spectra, called reference spectra, relating in particular to particular compounds in the effluent under study.

That method therefore assumes a prior knowledge of the composition of the effluent or of the compounds liable to be found in it, which requires laboratory analyses beforehand. Moreover, a library of compound spectra or predetermined composition spectra must be established beforehand.

The document EP 1 070 954 refers to the use of spectroscopy in the visible-UV spectrum to determine global parameters by deconvolution of spectra. That document proposes monitoring of the effluent overtime to determine the precise moment at which possible pollution begins to be manifested. That method therefore requires, at each site at which measurements are effected, prior characterization of the effluent by conventional methods and prior calibration and identification of reference spectra specific to the effluent being analyzed.

Known qualification methods are therefore totally tied to the environment in which they are used. In particular, in VIS-UV spectrophotometry, it is assumed that the effluent absorbs in the range of wavelengths concerned.

Another drawback of prior art methods is that they are not capable of processing other types of measurements, such as pH, conductivity, or temperature measurements in particular.

One object of the present invention is to propose a method of qualifying the variability of the composition of an effluent in which a succession of measurements is effected over time of at least one first physical-chemical parameter and one second physical-chemical parameter of the effluent, which method is independent of the environment in which it is used and just as capable of processing parametric measurements as non-parametric measurements.

The invention achieves its object by the following actions at each time step:

determining a first derivative for each of the first and second parameters;

determining at least one second derivative between the first and second parameters;

defining first logical domains for the first derivative of each of the parameters comprising at least one normal first logical domain corresponding to a normal variability of said first derivative and one abnormal first logical domain corresponding to an abnormal variability of said first derivative;

assigning first probabilities of the first derivative of each of the parameters belonging to each of the first logical domains;

defining second logical domains comprising at least one normal second logical domain corresponding to a normal variability of said second derivative and one abnormal second logical domain corresponding to an abnormal variability of said second derivative;

assigning second probabilities of the second derivative belonging to each of the second logical domains;

defining global logical domains on the basis of the first and second logical domains, the global logical domains comprising at least one normal global logical domain and one abnormal global logical domain;

assigning global probabilities of the combination of the first derivatives of the parameters and at least one second derivative belonging to each of the global logical domains; and qualifying the variability of the composition of the effluent on the basis of said global probabilities.

Accordingly, by means of the invention, it is not necessary to know the "usual" composition of the effluent beforehand to be able to detect an anomaly in the variability of its composition.

Moreover, by means of the invention, nor is it necessary to carry out analyses beforehand in order to initialize the method.

To the contrary, the method of the invention requires only a temporal succession of measurements of parameters to adapt to the environment in which it is used, which environment can be an effluent disposal network, for example, or a drinking water network, or an industrial site.

This means that the method of the present invention is simple and quick to use, requiring no preliminary steps of calibration or laboratory analysis like those that have to be effected when using the known methods.

Furthermore, the method of the invention can advantageously be based as much on analyzing the variability of spectrum measurements as on analyzing the variability of measurements of magnitudes such as, for example but not exclusively, pH, Redox potential, conductivity, or temperature.

One of the principal objectives of the invention is to advise the operator immediately and in real time of the possible arrival of effluent having a hazardous composition.

To this end, the evolution of the variation of each of the individual parameters taken is analyzed, and also the evolution of the relative variation between the first and second parameters.

In the meaning of the present invention, the first derivatives are relative to the same magnitude, preferably time, whereas the second derivatives denote the variation of one of the parameters relative to the other, preferably over time.

If the parameter depends on a non-temporal variable, the second derivative can for example be the derivative of the parameter relative to said variable for a given time step.

In other words, the way each of the parameter evolves, preferably over time, is analyzed using the first derivatives. This yields the individual variances of the parameters, the first derivative advantageously being a time derivative.

In contrast, the way the parameters evolve relative to each other is analyzed using the second derivatives.

This is referred to herein as the cross variance of said parameters.

Cross variances are used in particular to determine whether the parameters evolve in a way that is similar, or at least correlated.

The number of parameters is preferably significantly greater than two.

There are preferably as many second derivatives as there are combinations of parameters.

The underlying idea is to compare the individual variances and cross variances to establish an indication of the global variance of the composition of the effluent.

The mathematical processing for implementing the method of the invention is based on the theory of fuzzy logic, well known in other fields, and thus the comparison referred to above is effected by an inference operation, well known in other fields.

As a function of the global variance indication, the variation of the composition of the effluent can be qualified as normal or abnormal, or by any other appropriate qualifier.

To be more precise, assigning the first probabilities of the first derivative of each of the parameters belonging to each of the first logical domains characterizes the individual variances of the parameters, whereas assigning the second probabilities of the second derivatives belonging to each of the second logical domains characterizes the cross variances of the parameters.

Finally, it is clear that the step of assigning said global probabilities characterizes the global variance of the parameters.

The mathematical processing applied by the present invention preferably uses at least one variable-length moving database consisting of the values of the parameters in preceding time steps, whereby the method adapts on its own to natural evolution of the effluent.

A moving database is one that contains a predetermined number of values, the placing of a new entry in the database entailing the deletion of the oldest stored value.

This implies that the operator does not have to set thresholds to determine whether the effluent varies or to adapt any such threshold to the natural evolution of the effluent, which is particularly beneficial.

To the contrary, by means of the invention, the method determines such thresholds automatically, as a function of the data stored in the database.

As mentioned above, the method of the invention does not require any measurement of the effluent in the laboratory, beforehand or otherwise. Moreover, no prior calibration of the mathematic tool used is necessary.

This eliminates the need for measurements targeted on certain characteristics of the effluent, and so the method of the invention offers an overall approach to the hazard risk linked to the variability of the composition of the effluent.

Finally, a simple qualification criterion can be chosen, for example a "red light" indicating that the effluent has varied strongly, this implying a high risk of malfunction of the treatment, and associated for example with a "green light" signifying that the effluent has varied little or not at all.

For the first derivative of each of the parameters, the first logical domains are advantageously defined on the basis of a multiple of the standard deviation evaluated from a set consisting of values of the first derivative of said parameter determined in preceding time steps.

For the first derivative of each of the parameters, the first logical domains are preferably also defined on the basis of the mean or median value of a set consisting of values of the first derivative of said parameter determined in preceding time steps.

The second logical domains are advantageously defined on the basis of a multiple of the standard deviation evaluated on the basis of a set consisting of values of said at least one second derivative determined in preceding time steps.

The global logical domains are advantageously defined on the basis of a multiple of the standard deviation evaluated on the basis of a set consisting of the values of the first derivatives of the parameters and values of said at least one second derivative determined in preceding time steps.

The values determined in above-mentioned preceding time steps are advantageously stored in at least one moving database, such as that referred to above.

To refine the qualification of the variability of the composition of the effluent, for the first derivative of each of the parameters, a first intermediate logical domain is defined corresponding to a subnormal variability of said first derivative.

For said at least one second derivative, a second intermediate logical domain is defined corresponding to a subnormal variability of said second derivative.

Additionally, one or more global intermediate logical domains corresponding to a highly-abnormal variation of the composition of the effluent can also be defined.

In practice, an "amber light" can be used in addition to the red light and the green light referred to above, said amber light reflecting a variation of the effluent in an acceptable range, the risk being estimated as moderate but requiring increased vigilance (potential risk of evolution toward a red light).

In a first implementation, said global probabilities are calculated on the basis of a weighted sum of said first and second probabilities.

In a second implementation:
third logical domains comprising at least a normal third logical domain and an abnormal third logical domain are defined, the third logical domains being defined on the basis of the first logical domains;

fourth logical domains comprising at least a normal fourth logical domain and an abnormal fourth logical domain are defined, the fourth logical domains being defined on the basis of the second logical domains;

third probabilities of a set consisting of the first derivatives of the parameters belonging to each of the third logical domains are assigned;

fourth probabilities of a set consisting at least of said at least one second derivative belonging to each of the fourth logical domains are assigned;

the global logical domains are defined on the basis of the third and fourth logical domains.

In the second implementation, additional third and fourth logical domains are inserted to refine the qualification of the variability of the composition of the effluent and to prevent false alarms.

Preferably, the normal third logical domain corresponds to the union of the normal first logical domains, the abnormal third logical domain corresponds to the union of the abnormal first logical domains, the normal fourth logical domain corresponds to the union of the normal second logical domains, and the abnormal fourth logical domain corresponds to the union of the abnormal second logical domains.

There are advantageously defined a subnormal third logical domain that preferably corresponds to the union of the subnormal first logical domains and a subnormal fourth logical domain that preferably corresponds to the union of the subnormal second logical domains.

Five global logical domains are preferably defined.

The first global logical domain preferably corresponds to the union of the normal third logical domain and the normal fourth logical domain.

The second global logical domain preferably corresponds to the union of the union of the normal third logical domain and the subnormal fourth logical domain and the union of the subnormal third logical domain and the normal fourth logical domain.

The third global logical domain preferably corresponds to the union of the union of the normal third logical domain and the abnormal fourth logical domain with the union of the subnormal third logical domain and the subnormal fourth logical domain and the union of the abnormal third logical domain and the normal fourth logical domain.

The fourth global logical domain preferably corresponds to the union of the union of the subnormal third logical domain and the abnormal fourth logical domain and the union of the abnormal third logical domain and the subnormal fourth logical domain.

The fifth global logical domain preferably corresponds to the union of the abnormal third logical domain and the abnormal fourth logical domain.

Finally, after they have been calculated, overall probabilities of the set consisting of the first derivatives of the parameters and the second derivatives belonging the global logical domains are assigned.

Said global probabilities are advantageously calculated on the basis of a weighted sum of said third and fourth probabilities.

Said weighted sum preferably involves at least one dynamic weighting coefficient, for example the standard deviation evaluated from a set consisting of values of the first derivative determined in preceding time steps.

In a first variant, the global logical domain qualifying the variability of the composition of the effluent is that having the maximum global probability.

Preferably, only the fifth global logical domain is used to determine the variability of the composition of the effluent.

Clearly this fifth global domain is that for which the probability of a particularly abnormal variability of the composition of the effluent is the strongest.

In a second variant, the global logical domain qualifying the variability of the composition of the effluent is the most abnormal logical domain for which said global probability is non-zero.

In a third variant, the global logical domain qualifying the variability of the composition of the effluent is the most abnormal logical domain for which said global probability is above a predetermined threshold.

In a preferred implementation of the invention, the first parameter is the absorbance of the effluent measured at a first wavelength.

Each of the parameters is preferably the absorbance of the effluent at a given wavelength.

The absorbance of the effluent is preferably measured in each time step at a plurality of wavelengths, preferably wavelengths in the range 200 nanometers (nm) to 700 nm.

The first derivative is advantageously a derivative of the absorbance relative to time for a given wavelength and the second derivative is advantageously a derivative of the absorbance relative to wavelength calculated in a given time step.

The present invention also provides a device for tracking the variability of the composition of an effluent by using the method of the present invention.

Other features and advantages of the invention become more apparent on reading the following description of an implementation of the invention given by way of non-limiting example.

The description refers to the appended figures, in which.

A preferred implementation of the method of the present invention, the objective of which is to evaluate the variability over time of the composition of a chemicals industry effluent, is described in more detail below with the assistance of FIGS. 1 to 4.

Figure 1:
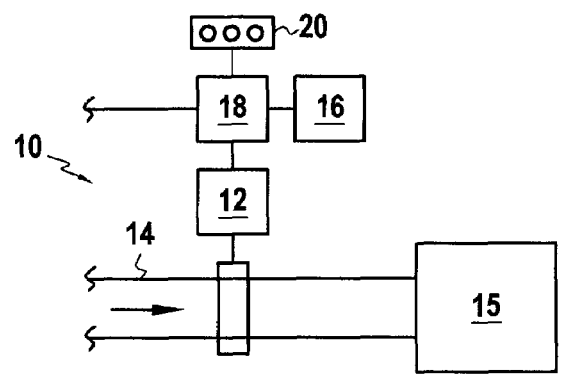
FIG. 1 is a diagram representing a device for monitoring the variability of the composition of an effluent using the method of the present invention.

FIG. 1 shows a device 10 of the invention using the method of the invention.

As seen in this figure, the device 10 includes measuring means 12 for measuring the absorbance of the effluent flowing in a pipe 14, which is preferably but not essentially on the upstream side of an effluent treatment station 15.

The values measured by the measuring means 12 are stored in storage means 16 and a microprocessor 18 effects calculations to qualify the variability of the composition of the effluent.

The result of the calculations is preferably given by a visual interface 20 comprising three colored lights, for example green, amber, and red lights, characterizing the variability of the effluent from the normal.

The method of the invention is explained in more detail below with the assistance of the FIG. 2 diagram.

In this implementation, a succession of measurements is effected over time, producing a plurality of parameters, namely the absorbance of the effluent at each of a plurality of wavelengths.

In other words, in each time step, during a step S101, the absorbance of the effluent is measured at wavelengths in the range 200 nm to 700 nm, preferably in the range 230 nm to 500 nm.

The measurements are preferably effected by varying the wavelength in steps of 1 nm and the time step t preferably lasts two hours.

Figure 2:
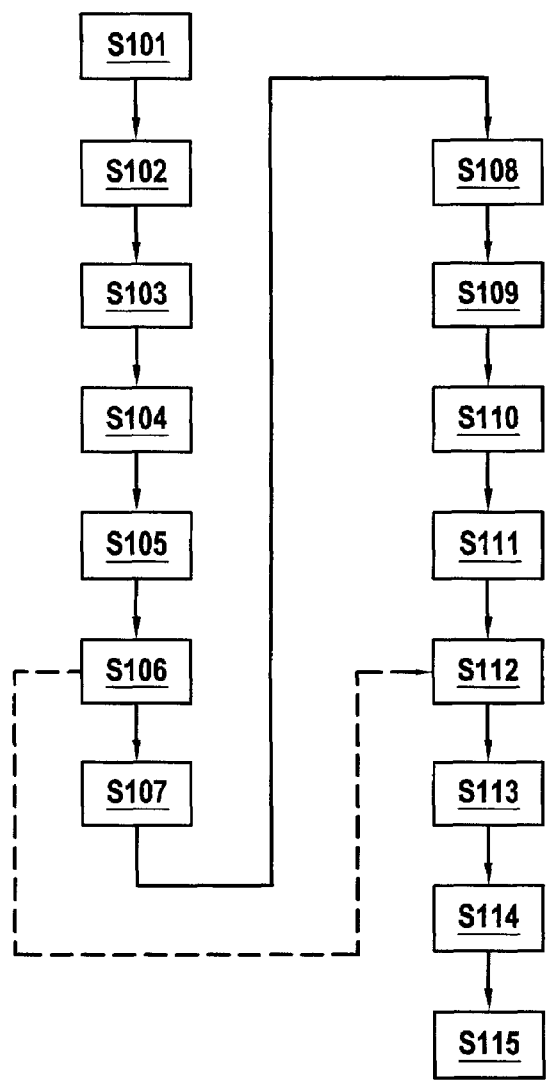
FIG. 2 is a diagram representing the steps of the preferred implementation of the present invention.

The FIG. 2 diagram represents the steps that are carried out in each time step.

Accordingly, in this implementation, in which the absorbance is measured at wavelengths in the range 230 nm to 500 nm, 271 parameters are measured simultaneously in the effluent every two hours. It is therefore clear that in the meaning of the invention the first parameter is the absorbance at the wavelength of 230 nm, the second parameter is the absorbance at the wavelength of 231 nm, and so on up to the $271^{st}$ parameter, which is the absorbance at 500 nm.

Obviously, the number of parameters is not limited to 271 and a different number of parameters can be selected without departing from the scope of the present invention. It is preferable, although not essential, for the storage means to include a database storing the parameter measurements for a plurality of time steps t.

During a second step S102, a first derivative is determined for each of the 271 parameters by calculating the difference between two consecutive absorbance values at the same wavelength and dividing the result by the time difference $\Delta t$ between the two measurements.

Accordingly, if the first parameter is considered, namely the absorbance Abs of the effluent at 230 nm, the first derivative $d_{1,1}(t)$ of the first parameter has the following expression:

$$d_{1,1}(t) = \frac{Abs_{230}(t) - Abs_{230}(t - \Delta t)}{\Delta t}$$

The same applies to the first derivative $d_{1,2}(t)$ of the second parameter, which has the expression:

$$d_{1,2}(t) = \frac{Abs_{231}(t) - Abs_{231}(t - \Delta t)}{\Delta t}$$

And so on up to the $271^{st}$ parameter.

During a third step S103 at least one second derivative between the parameters is determined.

To be more precise, in this example, 270 second derivatives of the 271 parameters are defined. The $1^{st}$ second derivative $d_{2,1}(t)$ is calculated as the difference between the absorbance values at 231 nm and at 230 nm, namely:

$$d_{2,1}(t) = \frac{Abs_{231}(t) - Abs_{230}(t)}{231 - 230}$$

It is therefore clear that the second derivative $d_{2,1}(t)$ is the relative difference between the parameters $Abs_{231}(t)$ and $Abs_{230}(t)$ and that the function $t \rightarrow d_{2,1}(t)$ gives the temporal variation of the relative difference between these two parameters.

The same applies to the $2^{nd}$ second derivative $d_{2,2}(t)$, which has the expression:

$$d_{2,2}(t) = \frac{Abs_{232}(t) - Abs_{231}(t)}{232 - 231}$$

and so on up to the $270^{th}$ second derivative.

In a fourth step S104, there are defined for each $j^{th}$ first derivative (j=1 to 271), i.e. for the first derivative of each of the parameters, three first logical domains ($DL_1^i(j)$, i=1 to 3, j=1 to 271) determined by the following calculations:

a) a mean $\overline{d_{1,j}}(t)$ and a standard deviation $\sigma_{d_{1,j}}(t)$ are calculated from the 50 previously calculated values of each $j^{th}$ first derivative (j=1 to 271):

$$\overline{d_{1,j}}(t) = \frac{1}{50} \sum_{i=0}^{49} d_{1,j}(t - i\Delta t)$$

and:

$$\sigma_{d_{1,j}}(t) = \sqrt{\frac{1}{49} \sum_{i=0}^{49} (d_{1,j}(t - i\Delta t) - \overline{d_{1,j}}(t))^2}$$

b) for each $j^{th}$ first derivative (j=1 to 271) the absolute difference $\epsilon_{1,j}(t)$ from the mean of the first derivatives is calculated:

$$\epsilon_{1,j}(t) = |d_{1,j}(t) - \overline{d_{1,j}}(t)|$$

c) the first logical domains $DL_1^i(j,t)$ (with i=1 to 3, j=1 to 271) are then defined as follows in the next time step t:

the $1^{st}$ first logical domain each $j^{th}$ first derivative "normal variation of the first derivative", $DL_1^1(j,t)$, is characterized in that: $\epsilon_{1,j}(t) < \sigma_{1,j}(t)$;

the $2^{nd}$ first logical domain of each $j^{th}$ first derivative "subnormal variation of the first derivative", $DL_1^2(j,t)$, is characterized in that: $\sigma_{1,j}(t) < \epsilon_{1,j}(t) < 2\sigma_{1,j}(t)$;

the $3^{rd}$ first logical domain of each $j^{th}$ first derivative "abnormal variation of the first derivative", $DL_1^3(j,t)$, is characterized in that: $\epsilon_{1,j}(t) > 2\sigma_{1,j}(t)$.

Figure 3:
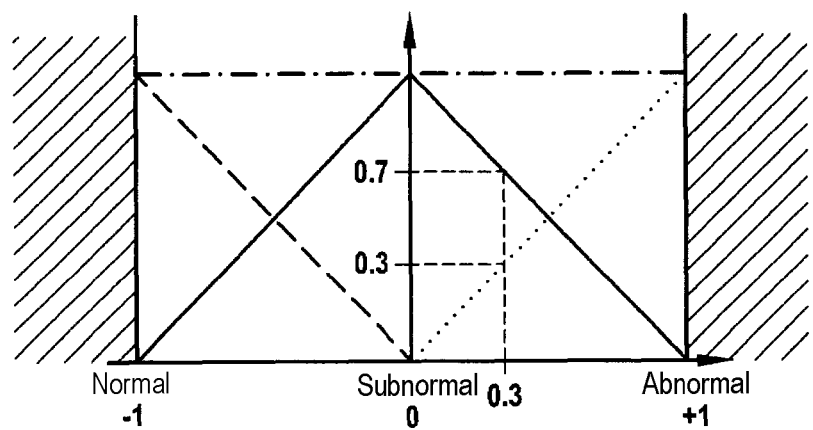
FIG. 3 is a graph representing triangle functions for determining the probabilities of the first derivatives belonging to the first logical domains.

During a fifth step S105, the probabilities $P(DL_1^i(j,t))$ (i=1 to 3, j=1 to 271) at time t of the 271 first derivatives belonging to each of the first logical domains are assigned by effecting the following sub-steps:

a) the absolute deviation obtained for each $j^{th}$ first derivative is normalized between −1 and 1, with the following correspondence:

if $\epsilon_{1,j}(t) = 0$ then $\|\epsilon_{1,j}(t)\| = -1$;

if $\epsilon_{1,j}(t) \geq 3\sigma_{1,j}(t) \cdot d_{1,j}(t)$ then $\|\epsilon_{1,j}(t)\| = +1$;

else $\|\epsilon_{1,j}(t)\| = -1 + \frac{2 \times \epsilon_{1,j}(t)}{3\sigma_{1,j}(t)}$ b) there follows fuzzyfication (i.e. the assignment of each $j^{th}$ first derivative belonging to the first logical domains $DL_1^i(j,t)$ of each normalized value $\|\epsilon_{1,j}(t)\|$ with triangle functions as represented in FIG. 3).

FIG. 3 represents the situation where, for the $50^{th}$ first derivative with a value of $\|\epsilon_{1,50}(t_0)\| = 0.3$ at time $t_0$, there are obtained $P(DL_1^1(50,t_0)) = 0$, $P(DL_1^2(50,t_0)) = 0.7$, $P(DL_1^3(50,t_0)) = 0.3$, which correspond to the probabilities of the $50^{th}$ first derivative belonging to the first logical domains.

During a sixth step S106, second logical domains are defined, namely, for each $k^{th}$ second derivative, three second logical domains ($DL_2^i(k,t)$, i=1 to 3 k=1 to 270), determined from the following calculations:

a) the mean and the standard deviation of the last 50 values of each second derivative are calculated:

$$\overline{d_{2,k}}(t) = \frac{1}{50}\sum_{i=0}^{49} d_{2,k}(t - i\Delta t)$$

and:

$$\sigma_{d_{2,k}}(t) = \sqrt{\frac{1}{49}\sum_{i=0}^{49}(d_{2,k}(t - i\Delta t) - \overline{d_{2,k}}(t))^2}$$

b) the absolute deviation $\epsilon_{2,k}(t)$ to the mean of the second derivatives is calculated for each $k^{th}$ second derivative:

$$\epsilon_{2,k}(t) = |d_{2,k}(t) - \overline{d_{2,k}}(t)|$$

c) the second logical domains $DL_2^i(k,t)$ are then defined as follows:

the $1^{st}$ second logical domain "normal variation of the $k^{th}$ second derivative", $DL_2^1(k,t)$, is characterized in that: $\epsilon_{2,k}(t) < \sigma_{2,k}(t)$;

the 2nd second logical domain "subnormal variation of the kth second derivative", $DL_2^2(k,t)$, is characterized in that: $\sigma_{2,k}(t) < \epsilon_{2,k}(t) < 2\sigma_{2,k}(t)$;

the $3^{rd}$ second logical domain "abnormal variation of the $k^{th}$ second derivative", $DL_2^3(k,t)$, is characterized in that: $\epsilon_{2,k}(t) > 2\sigma_{2,k}(t)$.

Figure 4:
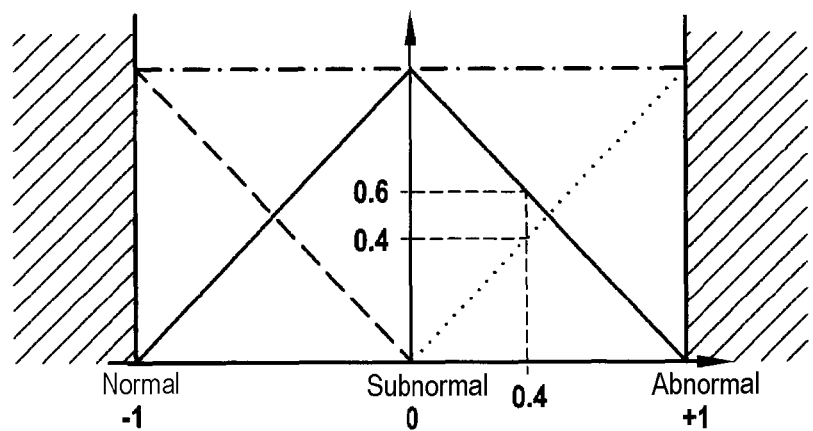
FIG. 4 is a graph representing triangle functions for determining the probabilities of the second derivatives belonging to the second logical domains.

During a seventh step S107, the probabilities $P(DL_2^i(k,t))$ (i=1 to 3, k=1 to 270) of the $k^{th}$ second derivatives belonging to the second logical domains are assigned by effecting the following sub-steps:

a) the absolute deviation obtained is normalized between −1 and 1, with the following correspondence:

$$\text{if } \varepsilon_{2,k}(t) = 0 \text{ then } \|\varepsilon_{2,k}(t)\| = -1;$$

$$\text{if } \varepsilon_{2,k}(t) \geq 3\sigma_{2,k}(t) \cdot d_{2,k}(t) \text{ then } \|\varepsilon_{2,k}(t)\| = +1;$$

$$\text{else } \|\varepsilon_{2,k}(t)\| = -1 + \frac{2 \times \varepsilon_{2,k}(t)}{3\sigma_{2,k}(t)}$$

b) there follows fuzzyfication (i.e. assigning the probabilities of each $k^{th}$ second derivative belonging to the second logical domains $DL_2^i(k,t)$ of each normalized value $\|\epsilon_{2,k}(t)\|$ with triangle functions as represented in FIG. 4.

FIG. 4 represents the situation where, for the $50^{th}$ second derivative with a value of $\|\epsilon_{2,50}(t_0)\|=0.4$ at time $t_0$, there are obtained $P(DL_2^1(50,t_0))=0$, $P(DL_2^2(50,t_0))=0.6$, $P(DL_2^3(50,t_0))=0.4$, which correspond to the probabilities of the $50^{th}$ second derivative belonging to the second logical domains.

During an eighth step S108, which is preferred but not essential, three logical domains are defined, namely three third logical domains ($DL_3^i(t)$, i=1 to 3) for the first derivatives, corresponding to:

a) for the $1^{st}$ third logical domain $DL_3^1(t)$, the union of normal $1^{st}$ first local domains;

b) for the $2^{nd}$ third logical domain $DL_3^2(t)$, the union of subnormal $2^{nd}$ first logical domains;

c) for the $3^{rd}$ third local domain $DL_3^3(t)$, the union of the abnormal $3^{rd}$ first local domains.

During a ninth step S109, also preferred but not essential, the probability of all the 271 first derivatives belonging to the third logical domains is calculated by summing the probabilities of each $j^{th}$ first derivative belonging to the first logical domains weighted by the standard deviation of the first derivatives (with i=1 to 3):

$$P(DL_3^i(t)) = \sum_{j=1}^{271} \sigma_{1,j}(t) \times P(DL_1^i(j,t))$$

During a tenth step S110, also preferred but not essential, fourth logical domains are defined, namely three fourth logical domains ($DL_4^i(t)$, i=1 to 3) for the second derivatives, and corresponding to:

a) for the $1^{st}$ fourth logical domain, $DL_4^1(t)$, the union of the normal $1^{st}$ second logical domains;

b) for the $2^{nd}$ fourth logical domain, $DL_4^2(t)$, the union of the subnormal $2^{nd}$ second logical domains;

c) for the $3^{rd}$ fourth logical domain, $DL_4^3(t)$, the union of the abnormal $3^{rd}$ second logical domains.

During an eleventh step S111, also preferred but not essential, the probability of each of the 270 second derivatives belonging to the three fourth logical domains is calculated by summing the probabilities of each $k^{th}$ second derivative belonging to the second logical domains weighted by the standard deviation of the second derivatives (with i=1 to 3):

$$P(DL_4^i(t)) = \sum_{k=1}^{270} \sigma_{2,k}(t) \times P(DL_2^i(k,t))$$

During a twelfth step S112, global logical domains are defined on the basis of the third and fourth logical domains and on the basis of which the global variability of the effluent will be defined, preferably five global logical domains ($DL_5^l(t)$, with l=1 to 5). They correspond to:

a) for the first global logical domain $DL_5^1(t)$, the union of the normal $1^{st}$ third logical domain and the normal $1^{st}$ fourth logical domain;

b) for the second global logical domain $DL_5^2(t)$, the union of the normal $1^{st}$ third logical domain and the subnormal $2^{nd}$ fourth logical domain and the union of the subnormal $2^{nd}$ third logical domain and the normal $1^{st}$ fourth logical domain;

c) for the third global logical domain $DL_5^3(t)$, the union of the normal $1^{st}$ third logical domain and the abnormal $3^{rd}$ fourth logical domain with the union of the subnormal $2^{nd}$ third logical domain and the subnormal $2^{nd}$ fourth logical domain and the union of the abnormal $3^{rd}$ third logical domain and the normal $1^{st}$ fourth logical domain;

d) for the fourth global logical domain $DL_5^4(t)$, the union of the union of the subnormal $2^{nd}$ third logical domain and the abnormal $3^{rd}$ fourth logical domain and the union of the abnormal $3^{rd}$ logical domain and the subnormal $2^{nd}$ fourth logical domain;

e) for the fifth global logical domain $DL_5^5(t)$, the union of the abnormal $3^{rd}$ third logical domain and the abnormal $3^{rd}$ fourth logical domain.

During a thirteenth step S113, global probabilities ($P(DL_5^l(t)$, with l=1 to 5) of the set consisting of the first derivatives of the parameters and the second derivatives belonging to each of the global logical domains ($DL_5^l(t)$, with l=1 to 5), are assigned, said probabilities preferably being calculated as follows:

$$P(DL_5^1(t)) = P(DL_3^1(t)) \times P(DL_4^1(t))$$

$$P(DL_5^2(t)) = [P(DL_3^2(t)) \times P(DL_4^1(t))] + [P(DL_3^1(t)) \times P(DL_4^2(t))]$$

$$P(DL_5^3(t))=[P(DL_3^3(t))\times P(DL_4^1(t))]+[P(DL_3^2(t))\times P(DL_4^2(t))]+[P(DL_3^1(t))\times P(DL_4^3(t))]$$

$$P(DL_5^4(t))=[P(DL_3^3(t))\times P(DL_4^2(t))]+[P(DL_3^2(t))\times P(DL_4^3(t))]$$

$$P(DL_5^5(t))=P(DL_3^3(t))\times P(DL_4^3(t))$$

During a fourteenth step S114, the result obtained is normalized by dividing each probability of belonging to the five global logical domains by the sum of those probabilities.

Then, during a fifteenth step S115, the variability of the composition of the effluent is qualified on the basis of the global probabilities, preferably using only the fifth global logical domain. The following tests are effected (for example):

- If the probability of belonging to the fifth global logical domain is above a first threshold, for example 66%, the composition of the effluent has varied strongly. A red light is displayed by the interface 20.
- If the probability of belonging to the fifth global logical domain is for example between 33% and 66%, the composition of the effluent has varied. An amber light is displayed by the interface 20.
- If the probability of belonging to the fifth global logical domain is below a second threshold, for example 33%, the composition of the effluent has not varied. A green light is displayed by the interface 20.

This non-limiting implementation minimizes false alarms, which is advantageous. It is necessary for a majority of the first and second derivatives to have high probabilities of belonging to the abnormal logical domains for the fifth global logical domain to have a strong probability of belonging and to trip an alarm.

As mentioned above, the steps S107 to S111 are not essential to implementation of the invention.

One variant of the invention defines the global logical domains directly from the first and second logical domains, without using third and fourth logical domains, assigning global probabilities of the set consisting of the first derivatives of the parameters and the second derivatives belonging to each of the global logical domains, then qualifies the variability of the composition of the effluent on the basis of the global probabilities in a similar way to the steps S112 to S115.

The invention claimed is:

1. A method of qualifying the variability of the composition of an effluent, in which a succession of measurements is effected over time of at least one first physical-chemical parameter and one second physical-chemical parameter of the effluent, comprising the following actions at each time step:
   determining a first derivative for each of the first and second parameters;
   determining at least one second derivative between the first and second parameters;
   defining first logical domains for the first derivative of each of the parameters comprising at least one normal first logical domain corresponding to a normal variability of said first derivative and one abnormal first logical domain corresponding to an abnormal variability of said first derivative;
   assigning first probabilities of the first derivative of each of the parameters belonging to each of the first logical domains;
   defining second logical domains comprising at least one normal second logical domain corresponding to a normal variability of said second derivative and one abnormal second logical domain corresponding to an abnormal variability of said second derivative;
   assigning second probabilities of the second derivative belonging to each of the second logical domains;
   defining global logical domains on the basis of the first and second logical domains, the global logical domains comprising at least one normal global logical domain and one abnormal global logical domain;
   assigning global probabilities of the combination of the first derivatives of the parameters and at least one second derivative belonging to each of the global logical domains; and
   qualifying the variability of the composition of the effluent on the basis of said global probabilities.

2. A qualification method according to claim 1, wherein, for the first derivative of each of the parameters, the first logical domains are defined on the basis of a multiple of the standard deviation evaluated from a set consisting of values of the first derivative of said parameter determined in preceding time steps.

3. A qualification method according to claim 1, wherein, for the first derivative of each of the parameters, the first logical domains are also defined on the basis of the mean or median value of a set consisting of values of the first derivative of said parameter determined in preceding time steps.

4. A qualification method according to claim 1, wherein the second logical domains are defined on the basis of a multiple of the standard deviation evaluated on the basis of a set consisting of values of said at least one second derivative determined in preceding time steps.

5. A qualification method according to claim 1, wherein the global logical domains are defined on the basis of a multiple of the standard deviation evaluated on the basis of a set consisting of the values of the first derivatives of the parameters and values of said at least one second derivative determined in preceding time steps.

6. A qualification method according to claim 1, wherein, for the first derivative of each of the parameters, a first intermediate logical domain is defined corresponding to a subnormal variability of said first derivative.

7. A qualification method according to claim 1, wherein, for said at least one second derivative, a second intermediate logical domain is defined corresponding to a subnormal variability of said second derivative.

8. A qualification method according to claim 1, wherein an intermediate global logical domain is defined.

9. A qualification method according to claim 1 wherein said global probabilities are calculated on the basis of a weighted sum of said first and second probabilities.

10. A qualification method according to claim 1, wherein:
    third logical domains comprising at least a normal third logical domain and an abnormal third logical domain are defined, the third logical domains being defined on the basis of the first logical domains;
    fourth logical domains comprising at least a normal fourth logical domain and an abnormal fourth logical domain are defined, the fourth logical domains being defined on the basis of the second logical domains;
    third probabilities of a set consisting of the first derivatives of the parameters belonging to each of the third logical domains are assigned;
    fourth probabilities of a set consisting at least of said at least one second derivative belonging to each of the fourth logical domains are assigned;
    the global logical domains are defined on the basis of the third and fourth logical domains.

11. A qualification method according to claim 10, wherein said global probabilities are calculated on the basis of a weighted sum of said third and fourth probabilities.

12. A qualification method according to claim 11, wherein said weighted sum involves at least one dynamic weighting coefficient.

13. A qualification method according to claim 1, wherein the global logical domain qualifying the variability of the composition of the effluent is that having the maximum global probability.

14. A qualification method according to claim 1, wherein the global logical domain qualifying the variability of the composition of the effluent is the most abnormal logical domain for which said global probability is non-zero.

15. A qualification method according to claim 1, wherein the global logical domain qualifying the variability of the composition of the effluent is the most abnormal logical domain for which said global probability is above a predetermined threshold.

16. A qualification method according to claim 1, wherein the first derivative is a time derivative.

17. A qualification method according to claim 1, wherein the first parameter is the absorbance of the effluent measured at a first wavelength.

18. A qualification method according to claim 1, wherein each of the parameters is the absorbance of the effluent at a given wavelength.

19. A qualification method according to claim 18, wherein the first derivative is a derivative of the absorbance relative to time for a given wavelength and the second derivative is a derivative of the absorbance relative to wavelength calculated in a given time step.

20. A device for monitoring the variability of the composition of an effluent using the method according to claim 1 and including measuring means, memory means, and a microprocessor.

\* \* \* \* \*